United States Patent
Abouabdellah et al.

(10) Patent No.: US 7,482,346 B2
(45) Date of Patent: Jan. 27, 2009

(54) DERIVATIVES OF ALKYLPIPERAZINE AND ALKYLHOMOPIPERAZINE-CARBOXYLATES, PREPARATION METHOD THEREOF AND USE OF SAME AS FATTY ACID AMIDO HYDROLASE ENZYME INHIBITORS

(75) Inventors: Ahmed Abouabdellah, Thiais (FR); Antonio Almario Garcia, Chatenay Malabry (FR); Christian Hoornaert, Antony (FR); Tak Adrien Li, Fontenay aux Roses (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/466,192

(22) Filed: Aug. 22, 2006

(65) Prior Publication Data

US 2007/0027141 A1      Feb. 1, 2007

Related U.S. Application Data

(63) Continuation of application No. PCT/FR2005/000450, filed on Feb. 25, 2005.

(30) Foreign Application Priority Data

Feb. 26, 2004   (FR)   .................... 04 01953

(51) Int. Cl.
*A61K 31/50*      (2006.01)
*A61K 31/501*     (2006.01)
*A61K 31/497*     (2006.01)
*A61K 31/4965*    (2006.01)
*C07D 403/00*     (2006.01)
*C07D 401/00*     (2006.01)
*C07D 241/04*     (2006.01)
*C07D 295/00*     (2006.01)

(52) U.S. Cl. .................. 514/252.12; 514/252.13; 514/252.14; 514/252.15; 514/253.01; 514/253.09; 514/253.1; 514/253.11; 514/254.01; 514/254.02; 514/254.03; 514/254.04; 514/254.05; 514/254.07; 514/255.03; 544/359; 544/360; 544/400

(58) Field of Classification Search ............ 514/252.12, 514/252.13, 252.14, 252.15, 253.01, 253.09, 514/253.1, 253.11, 254.01, 254.02, 254.03, 514/254.04, 254.05, 254.07, 255.03; 544/359, 544/360, 400

See application file for complete search history.

(56) References Cited

FOREIGN PATENT DOCUMENTS

| | | |
|---|---|---|
| DE | 19816889 | 10/1999 |
| WO | WO 97/14689 | * 4/1997 |
| WO | WO 01/72728 | 10/2001 |
| WO | WO 03/097573 | 11/2003 |
| WO | WO 2004/099176 | 11/2004 |

OTHER PUBLICATIONS

West, Anthony R., Solid State Chemistry and Its Applications, Wiley, New York, 1988, 358.*
Steffens, et al., Fatty Acid Amidohydrolase in Human Neocortex—Activity in Epileptic and Non-epileptic Brain Tissue and Inhibition by Putative Endocannabinoids, Neuroscience Letters, 385, 13-17 (2005).*

\* cited by examiner

*Primary Examiner*—Deepak Rao
*Assistant Examiner*—Erich A Leeser
(74) *Attorney, Agent, or Firm*—Craig M. Bell

(57) ABSTRACT

The present invention comprises alkylpiperazine- and alkylhomopiperazine carboxylates and their derivatives, methods for their preparation and the therapeutic use thereof as fatty acid amido hydrolase (FAAH) enzyme inhibitors. These derivatives exert various pharmacological activities by interacting, inter alia, with cannabinoid and vanilloid receptors. By inhibiting the metabolic activity of the FAAH enzyme, compounds often responsible for the onset of disease and other pathological conditions are not generated and the incidence of the disease is greatly reduced.

8 Claims, No Drawings

DERIVATIVES OF ALKYLPIPERAZINE AND ALKYLHOMOPIPERAZINE-CARBOXYLATES, PREPARATION METHOD THEREOF AND USE OF SAME AS FATTY ACID AMIDO HYDROLASE ENZYME INHIBITORS

CROSS-REFERENCE TO RELATED APPLICATIONS

This application is a continuation of International Application No. PCT/FR2005000450 filed on Feb. 25, 2005 which is incorporated herein by reference in its' entirety which also claims the benefit of priority of French Patent Application No.04/01953 filed on Feb. 26, 2004.

FIELD OF THE INVENTION

The present invention relates generally to enzyme inhibitors and their use in the treatment and therapy of a wide variety of diseases and degenerative conditions. More particularly, the present invention is directed towards the use of alkylpiperazine- and alkylhomopiperazine carboxylates, processes for their preparation and methods of use thereof as fatty acid amido hydrolase (FAAH) enzyme inhibitors in the treatment of arthritis, heart disease, cancer and the like and to their application in a wide variety of therapeutic regimens.

BACKGROUND OF THE INVENTION

Phenylalkylcarbamate derivatives, dioxane-2-alkylcarbamate derivatives and piperidinyl- and piperazinyl-alkylcarbamate derivatives, methods for their preparation and use are described respectively in the documents WO 2004/067498 A, WO 2004/020430 A and WO 2004/099176, wherein they are described as being useful inhibitors of the enzyme fatty acid amido hydrolase. (FAAH). These references and their teachings are hereby incorporated by reference herein.

There is still a need to find and develop compounds and compositions that will inhibit the enzyme FAAH. The compounds of the present invention have surprisingly and unexpectedly been found to meet this goal.

The fatty acid amido hydrolase enzyme (FAAH) (*Chemistry and Physics of Lipids,* (2000), 108, 107-121) catalyses the hydrolysis of endogenous derivatives of amides and of esters of various fatty acids such as N-arachidonoylethanolamine (anandamide), N-palmitoylethanolamine, N-oleoylethanolamine, oleamide or 2-arachidonoylglycerol. These derivatives exert various pharmacological activities by interacting, inter alia, with cannabinoid and vanilloid receptors.

The alkylpiperazine- and alkylhomopiperazine carboxylates compounds of the present invention block this degradation pathway and increase the tissue level of these endogenous substances. They can be used in this manner to prevent and treat pathologies in which endogenous cannabinoids and/or any other substrates metabolized by the FAAH enzyme are involved.

SUMMARY OF THE INVENTION

The present invention comprises alkylpiperazine- and alkylhomopiperazine carboxylates and their derivatives, methods for their preparation and the therapeutic use thereof as fatty acid amido hydrolase (FAAH) enzyme inhibitors. These derivatives exert various pharmacological activities by interacting, inter alia, with cannabinoid and vanilloid receptors. By inhibiting the metabolic activity of the FAAH enzyme, compounds often responsible for the onset of disease and other pathological conditions are not generated and the incidence of the disease is greatly reduced.

DETAILED DISCLOSURE OF THE INVENTION

Diseases and pathological conditions that often result from the presence of these compounds that are generated by the metabolic activity of the fatty acid amido hydrolase enzyme include but are not limited to, for example, the following:

pain, especially acute or chronic pain of the neurogenic type: migraine, neuropathic pain, including forms associated with the herpes virus and diabetes;

acute or chronic pain associated with inflammatory diseases: arthritis, rheumatoid arthritis, osteoarthritis, spondylitis, gout, vasculitis, Crohn's disease, irritable bowel syndrome; acute or chronic peripheral pain; dizziness, vomiting, nausea, especially those subsequent to chemotherapy;

eating disorders, especially anorexia and cachexia of various kinds;

neurological and psychiatric pathologies: shaking, dyskinesia, dystonia, spasticity, obsessive-compulsive behaviours, Tourette's syndrome, all forms of depression and anxiety of any kind and cause, mood disorders, psychoses; acute and chronic neurodegenerative diseases: Parkinson's disease, Alzheimer's disease, senile dementia, Huntington's chorea, lesions associated with cerebral ischemia and with cranial and medullary trauma; epilepsy;

sleep disorders, including sleep apnoea;

cardiovascular diseases, especially hypertension, cardiac arrhythmias, arteriosclerosis, heart attack, cardiac ischemias; renal ischemia; cancers: benign skin tumors, papillomas and brain tumors, prostate tumors, brain tumours (glioblastomas, medulloepitheliomas, medulloblastomas, neuroblastomas, tumors of embryonic origin, astrocytomas, astroblastomas, ependyomas, oligodendrogliomas, plexus tumors, neuroepitheliomas, epiphysial tumor, ependymoblastomas, malignant meningiomas, sarcomatoses, malignant melanomas, schwannomas);

disorders of the immune system, especially autoimmune diseases: psoriasis, lupus erythematosis, diseases of the connective tissue or collagen diseases, Sjögren's syndrome, ankylosing spondylarthritis, undifferentiated spondylarthritis, Behcet's disease, haemolytic autoimmune anemias, multiple sclerosis, amyotrophic lateral sclerosis, amyloses, transplant rejection, diseases affecting the plasmocytic line; allergic diseases:

immediate or delayed hypersensitivity, allergic rhinitis orconjunctivitis, hypersensitivity, allergic rhinitis or conjunctivitis, contact dermatitis; parasitic, viral or bacterial infectious diseases: AIDS, meningitis; inflammatory diseases, in particular joint diseases: arthritis, rheumatoid arthritis, osteoarthritis, spondylitis, gout, vasculitis, Crohn's disease, irritable bowel syndrome; osteoporosis; eye conditions: ocular hypertension, glaucoma;

pulmonary conditions: diseases of the respiratory tract, bronchospasm, coughing, asthma, chronic bronchitis, chronic obstruction of the respiratory tract gastrointestinal diseases:

irritable bowel syndrome, inflammatory intestinal disorders, ulcers, diarrhea; urinary incontinence and bladder inflammation.

There is still a need to find and to develop pharmaceutical actives and composition formulations containing the same which inhibit the enzyme fatty acid amido hydrolase (FAAH) enzyme and consequently the diseases believed to be a result of the enzymes' metabolic action. Any one of the compounds of the present invention possess the ability to inactivate the metabolic action of this enzyme to achieve this and successfully treat the diseases that are a result of the presence of its' metabolites.

The compounds of the invention are of the generic formula (I)

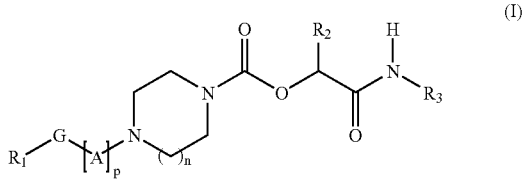

in which
n represents an integer 1 or 2;
p represents an integer ranging from 1 to 7;
A is selected from one or more groups X, Y and/or Z;
X represents a methylene group optionally substituted by one or two $C_{1-6}$-alkyl, $C_{3-7}$-cycloalkyl or $C_{3-7}$-cycloalkyl-$C_{1-3}$-alkylene groups;
Y represents either a $C_2$-alkenylene group optionally substituted by one or two $C_{1-6}$-alkyl, $C_{3-7}$-cycloalkyl or $C_{3-7}$-cycloalkyl-$C_{1-3}$-alkylene groups; or a $C_2$-alkynylene group;
Z represents a group of formula:

 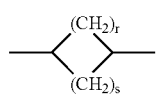

o represents an integer ranging from 1 to 5;
r and s represent integers and are defined such that r+s is a number ranging from 1 to 5;
G represents a single bond, an oxygen or sulphur atom or an SO, $SO_2$, C=O or CH(OH) group;
$R_1$ represents a group $R_4$ optionally substituted by one or more groups $R_5$ and/or $R_6$;
$R_4$ represents a group selected from a phenyl, pyridinyl, pyrimidinyl, pyridazinyl, pyrazinyl, triazinyl, pyrrolyl, furanyl, thienyl, imidazolyl, oxazolyl, thiazolyl, pyrazolyl, isoxazolyl, isothiazolyl, oxadiazolyl, thiadiazolyl, triazolyl, tetrazolyl, naphthalenyl, diphenylmethyl, quinolinyl, tetrahydroquinolinyl, isoquinolinyl, tetrahydroisoquinolinyl, quinazolinyl, quinoxalinyl, phthalazinyl, cinnolinyl, naphthyridinyl, benzofuranyl, dihydrobenzofuranyl, benzothienyl, dihydrobenzothienyl, indolyl, indolinyl, indanyl, indazolyl, isoindolyl, benzimidazolyl, benzoxazolyl, benzisoxazolyl, benzothiazolyl, benzisothiazolyl, benzotriazolyl, benzoxadiazolyl, benzothiadiazolyl, pyrrolopyridinyl, furopyridinyl, thienopyridinyl, imidazopyridinyl, oxazolopyridinyl, thiazolopyridinyl, pyrazolopyridinyl, isoxazolopyridinyl and isothiazolopyridinyl;
$R_5$ represents a halogen atom or a cyano, nitro, $C_{1-6}$-alkyl, $C_{1-6}$-alkoxy, hydroxyl, $C_{1-6}$-thioalkyl, $C_{1-6}$-fluoroalkyl, $C_{1-6}$-fluoroalkoxy or $C_1$-$C_6$-fluorothioalkyl group, a group $NR_7R_8$, $NR_7COR_8$, $NR_7CO_2R_8$, $NR_7SO_2R_8$, $COR_7$, $CO_2R_7$, $CONR_7R_8$, $SO_2R_7$ or $SO_2NR_7R_8$, or an —O—($C_{1-3}$-alkylene)-O group;
$R_6$ represents a phenyl, phenyloxy, benzyloxy, naphthalenyl, pyridinyl, pyrimidinyl, pyridazinyl or pyrazinyl group, the group or groups $R_6$ being optionally substituted by one or more groups $R_5$ identical to or different from one another;

$R_7$ and $R_8$ represent independently of one another a hydrogen atom or a $C_{1-6}$-alkyl group, or form with the atom or atoms which carry them a ring selected from azetidine, pyrrolidine, piperidine, morpholine, thiomorpholine, azepine and piperazine, this ring being optionally substituted by a $C_{1-6}$-alkyl or benzyl group;
$R_2$ represents a hydrogen atom or a $C_{1-6}$-alkyl group;
$R_3$ represents a hydrogen atom or a $C_{1-6}$-alkyl, $C_{3-7}$-cycloalkyl or $C_{3-7}$-cycloalkyl-$C_{1-3}$-alkyl group.

In the context of the invention the compounds of general formula (I) may therefore comprise two or more groups A identical to or different from another.

Among the compounds of generic formula (I) a first subgroup of compounds is composed of the compounds for which:
n represents an integer 1 or 2;
p represents an integer ranging from 1 to 7;
A is selected from one or more groups X and/or Y;
X represents a methylene group optionally substituted by one or two $C_{1-6}$-alkyl, more particularly methyl, groups;
Y represents either a $C_2$-alkenylene group or a $C_2$-alkynylene group;
G represents a single bond, an oxygen atom or a C=O group;
$R_1$ represents a group $R_4$ optionally substituted by one or more groups $R_5$ and/or $R_6$;
$R_4$ represents a group selected from a phenyl, naphthalenyl, diphenylmethyl, quinolinyl, indolyl, pyrazolyl, isoxazolyl, pyrimidinyl and thiazolyl;
$R_5$ represents a halogen atom, more particularly a chlorine, a fluorine, a bromine or an iodine, or a cyano group, a $C_{1-6}$-alkyl group, more particularly a methyl, an isopropyl or a tert-butyl, a $C_{1-6}$-alkoxy group, more particularly a methoxy, a $C_{1-6}$-fluoroalkyl group, more particularly a trifluoromethyl, a $C_1$-$C_6$-fluoroalkoxy group, more particularly a trifluoromethoxy, or an —O—($C_{1-3}$-alkylene)-O group, more particularly an —OCH$_2$O—;
$R_6$ represents a phenyl, naphthalenyl or benzyloxy group;
$R_2$ represents a hydrogen atom or a $C_{1-6}$-alkyl group;
$R_3$ represents a hydrogen atom or a $C_{1-6}$-alkyl, $C_{3-7}$-cycloalkyl or $C_{3-7}$-cycloalkyl-$C_{1-3}$- alkyl group.

Among the compounds of generic formula (I) a second preferred subgroup is comprised of the compounds for which:
n represents an integer 1;
p represents an integer ranging from 1 to 4;
A is selected from one or more groups X and/or Y;
X represents a methylene group optionally substituted by one or two $C_{1-6}$-alkyl, more particularly methyl, groups;
Y represents a $C_2$-alkynylene group;
G represents a single bond or an oxygen atom;
$R_1$ represents a group $R_4$ optionally substituted by one or more groups $R_5$ and/or $R_6$;
$R_4$ represents a group selected from a phenyl, naphthalenyl or isoxazolyl;
$R_5$ represents a halogen atom, more particularly a chlorine or a fluorine, or a cyano group, a $C_{1-6}$-alkoxy group, more particularly a methoxy, a $C_{1-6}$-fluoroalkyl group, more particularly a trifluoromethyl;
$R_6$ represents a phenyl group;
$R_2$ represents a hydrogen atom or $C_{1-6}$-alkyl group;
$R_3$ represents a hydrogen atom or a $C_{1-6}$-alkyl, $C_{3-7}$-cycloalkyl or $C_{3-7}$-cycloalkyl-$C_{1-3}$-alkyl group.

Among the compounds of generic formula (I) a third preferred subgroup of compounds is comprised of the compounds for which:
n, p, A, X, Y, Z, o, r, s, G, $R_1$, $R_4$, $R_5$, $R_6$, $R_7$ and $R_8$ are as defined in the generic formula (I) or in the subgroups as defined above;

R$_2$ represents a hydrogen atom;

R$_3$ represents a hydrogen atom or a C$_{1-6}$-alkyl group, more particularly a methyl, a C$_{3-7}$-cycloalkyl group, more particularly a cyclopropyl or a C$_{3-7}$-cycloalkyl-C$_{1-3}$-alkyl group, more particularly a —CH$_2$-cyclopropyl.

Among the compounds of generic formula (I) mention may be made of the following compounds:

2-(methylamino)-2-oxoethyl 4-(2-biphenyl-3-ylethyl)piperazine-1-carboxylate 2-(methylamino)-2-oxoethyl 4-(2-biphenyl-4-ylethyl)piperazine-1-carboxylate 2-(methylamino)-2-oxoethyl 4-[2-(1-naphthyl)ethyl]piperazine-1-carboxylate 2-(methylamino)-2-oxoethyl 4-{2-[3-(4-chlorophenyl)isoxazol-5-yl]ethyl}piperazine-1-carboxylate 2-(methylamino)-2-oxoethyl 4-{2-[5-(4-chlorophenyl)isoxazol-3-yl]ethyl}piperazine-1-carboxylate 2-(methylamino)-2-oxoethyl 4-(3-biphenyl-3-ylpropyl)piperazine-1-carboxylate 2-(methylamino)-2-oxoethyl 4-(3-biphenyl-4-ylpropyl)piperazine-1-carboxylate 2-(methylamino)-2-oxoethyl 4-(3-biphenyl-3-yl-1,1-dimethylpropyl)piperazine-1-carboxylate 2-(methylamino)-2-oxoethyl 4-[3-(3'-chlorobiphenyl-3-yl)propyl]piperazine-1-carboxylate 2-(methylamino)-2-oxoethyl 4-[3-(4'-chlorobiphenyl-3-yl)propyl]piperazine-1-carboxylate 2-(methylamino)-2-oxoethyl 4-[3-(3'-methoxybiphenyl-3-yl)propyl]piperazine-1-carboxylate 2-(methylamino)-2-oxoethyl 4-[3-(4'-methoxybiphenyl-3-yl)propyl]piperazine-1-carboxylate 2-(methylamino)-2-oxoethyl 4-[3-(3'-chlorobiphenyl-4-yl)propyl]piperazine-1-carboxylate 2-(methylamino)-2-oxoethyl 4-[3-(4'-chlorobiphenyl-4-yl)propyl]piperazine-1-carboxylate 2-(methylamino)-2-oxoethyl 4-[3-(2-naphthyl)propyl]piperazine-1-carboxylate 2-(methylamino)-2-oxoethyl 4-{3-[5-(4-chlorophenyl)isoxazol-3-yl]propyl}piperazine-1-carboxylate 2-(methylamino)-2-oxoethyl 4-{3-[3-(4-chlorophenyl)isoxazol-5-yl]propyl}piperazine-1-carboxylate 2-(methylamino)-2-oxoethyl 4-[4-(3-chlorophenyl)butyl]piperazine-1-carboxylate 2-(methylamino)-2-oxoethyl 4-[4-(4-chlorophenyl)butyl]piperazine-1-carboxylate 2-(methylamino)-2-oxoethyl 4-{4-[3-(trifluoromethyl)phenyl]butyl}piperazine-1-carboxylate 2-(methylamino)-2-oxoethyl 4-{4-[4-(trifluoromethyl)phenyl]butyl}piperazine-1-carboxylate 2-(methylamino)-2-oxoethyl 4-{4-[4-(trifluoromethylphenyl]but-3-yn-1-yl}piperazine-1-carboxylate 2-(methylamino)-2-oxoethyl 4-[5-(3-chlorophenyl)pent-4-yn-1-yl]piperazine-1-carboxylate 2-(methylamino)-2-oxoethyl 4-[5-(2,4-dichlorophenyl)pent-4-yn-1-yl]piperazine-1-carboxylate 2-(methylamino)-2-oxoethyl 4-[5-(2,5-dichlorophenyl)pent-4-yn-1-yl]piperazine-1-carboxylate 2-(methylamino)-2-oxoethyl 4-[5-(3,4-dichlorophenyl)pent-4-yn-1-yl]piperazine-1-carboxylate 2-(methylamino)-2-oxoethyl 4-[5-(3-chloro-4-fluorophenyl)pent-4-yn-1-yl]piperazine-1-carboxylate 2-(methylamino)-2-oxoethyl 4-[3-(2-chlorophenoxy)propyl]piperazine-1-carboxylate 2-(methylamino)-2-oxoethyl 4-[3-(3-chlorophenoxy)propyl]piperazine-1-carboxylate 2-(methylamino)-2-oxoethyl 4-[3-(4-chlorophenoxy)propyl]piperazine-1-carboxylate 2-(methylamino)-2-oxoethyl 4-[3-(2,3-dichlorophenoxy)propyl]piperazine-1-carboxylate 2-(methylamino)-2-oxoethyl 4-[3-(2,4-dichlorophenoxy)propyl]piperazine-1-carboxylate 2-(methylamino)-2-oxoethyl 4-[3-(2,5-dichlorophenoxy)propyl]piperazine-1-carboxylate 2-(methylamino)-2-oxoethyl 4-[3-(2,6-dichlorophenoxy)propyl]piperazine-1-carboxylate 2-(methylamino)-2-oxoethyl 4-[3-(3,5-dichlorophenoxy)propyl]piperazine-1-carboxylate.

The compounds of generic formula (I) may include one or more asymmetric carbons. They may exist in the form of enantiomers or diastereoisomers. The compounds of general formula (I) may also exist in the form of cis (Z) or trans (E) stereoisomers. These stereoisomers, enantiomers and diastereoisomers, and mixtures thereof, including the racemic mixtures, also fall within the claimed scope of the present invention.

The compounds of formula (I) may exist in the form of bases or of addition salts with acids. Addition salts formed in this manner are particularly preferred due to their enhanced solubility.

These salts are prepared using pharmaceutically acceptable acids, although the salts of other acids are useful, for example, for purifying and/or isolating compounds of formula (I).

The compounds of generic formula (I) may also be in the form of hydrates or solvates, namely in the form of associations or combinations with one or more molecules of water or a different solvent. Hydrates and solvates of this kind likewise fall within the scope of the invention.

In the context of this application and the claimed invention, the following terms are to be construed in light of their meanings as defined below:

C$_{t-z}$, where t and z may take the values from 1 to 7, is a carbon chain which may have from t to z carbon atoms; for example, C$_{1-3}$ is a carbon chain which may have 1 to 3 carbon atoms;

alkyl is a linear or branched saturated aliphatic group; for example, a C$_{1-6}$-alkyl group represents a carbon chain of 1 to 6 carbon atoms which is linear or branched, more particularly a methyl, ethyl, propyl, isopropyl, butyl, isobutyl, tert-butyl, pentyl or hexyl;

alkylene is a linear or branched, saturated divalent alkyl group; for example, a C$_{1-3}$-alkylene group represents a divalent carbon chain of 1 to 3 carbon atoms which is linear or branched, more particularly methylene, ethylene, 1-methylethylene or propylene;

cycloalkyl is a cyclic alkyl group; for example, C$_{3-7}$-cycloalkyl group represents a cyclic carbon group of 3 to 7 carbon atoms, more particularly a cyclopropyl, cyclobutyl, cyclopentyl, cyclohexyl or cycloheptyl;

alkenylene is a divalent unsaturated aliphatic group having 2 carbons, more particularly an ethylene, C$_2$-alkynylene is a —C≡C— group;

alkoxy is an —O-alkyl group having a linear or branched, saturated aliphatic chain;

thioalkyl is an —S-alkyl group having a linear or branched, saturated aliphatic chain;

fluoroalkyl is an alkyl group of which one or more hydrogen atoms have been substituted by a fluorine atom;

fluoroalkoxy is an alkoxy group of which one or more hydrogen atoms have been substituted by a fluorine atom;

fluorothioalkyl is a thioalkyl group of which one or more hydrogen atoms have been substituted by a fluorine atom; and a halogen atom is a fluorine, a chlorine, a bromine or an iodine.

The compounds of the invention may be prepared according to various methods, which are illustrated by the schemes which follow.

Thus according to a first method (scheme 1) the compounds of general formula (I) may be prepared by reacting an amine of general formula (IV), in which $R_1$, G, A, p and n are as defined in the general formula (I), with a carbonate of general formula (IIIa), in which V represents a hydrogen atom or nitro group, $R_2$ is as defined in the general formula (I) and R represents a methyl or ethyl group. The carbamate-ester of general formula (II) thus obtained is subsequently converted into a compound of general formula (I) by aminolysis using an amine of general formula $R_3NH_2$, in which $R_3$ is as defined in the general formula (I). The aminolysis reaction may be carried out in a solvent such as methanol or ethanol or in a mixture of solvents such as methanol and tetrahydrofuran.

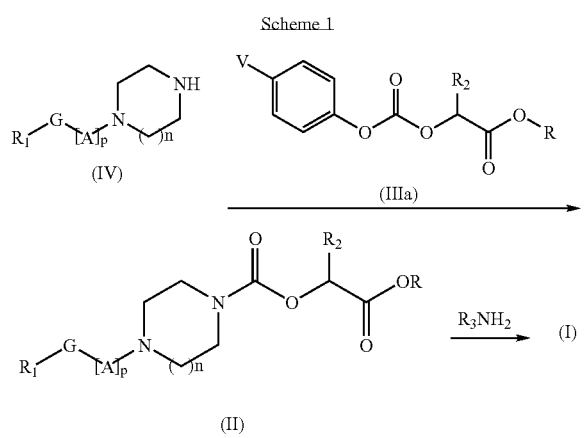

Another method (scheme 2) of obtaining compounds of general formula (I) involves reacting a piperazine or homopiperazine derivative of general formula (VII), in which PG represents a protective group such as a tert-butyloxycarbonyl (Boc), with a carbonate of general formula (IIIb), in which V represents a hydrogen atom or a nitro group and $R_2$ and $R_3$ are as defined in the general formula (I), then deprotecting the resultant compound, in the presence for example of a solution of hydrochloric acid in a solvent such as isopropanol. The carbamate-amide of general formula (V) thus obtained is subsequently converted into a compound of general formula (I) by reaction with a derivative of general formula (VI), in which $R_1$, G, p and A are as defined in the general formula (I) and W represents a chlorine, bromine or iodine atom or a mesylate or tosylate group. The N-alkylation reaction may be carried out in a solvent such as acetonitrile or toluene in the presence of a base such as potassium carbonate or diisopropylethylamine.

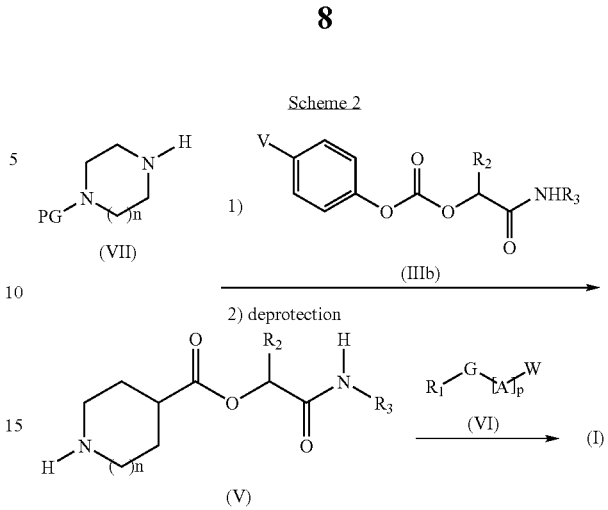

The compounds of general formula (I), (II) and (IV), in which $R_1$ represents a group of aryl-aryl, aryl-heteroaryl, heteroaryl-aryl or heteroaryl-heteroaryl type may also be prepared by reacting corresponding compounds of general formula (I), (II) or (IV) for which $R_4$ is substituted by a chlorine, bromine or iodine atom or by a triflate group, in the position where the group $R_6$ is to be introduced, with an aryl- or heteroaryl-boronic acid derivative in accordance with the Suzuki reaction conditions (Chem. Rev. 1995, 95, 2457-2483) or with an aryl- or heteroaryl-trialkylstannane derivative in accordance with the Stille reaction conditions (Angew. Chem. Int. Ed. 1986, 25, 504-524).

The carbonates of general formula (IIIa) and (IIIb) may be prepared according to any method described in the literature, for example by reacting an alcohol of respective general formula $HOCHR_2COOR$ where R represents a methyl or ethyl group, or $HOCHR_2CONHR_3$ where $R_3$ is as defined in the general formula (I), with phenyl chloroformate or 4-nitrophenyl chloroformate, in the presence of a base such as triethylamine or diisopropylethylamine.

The compounds of general formula (IV), (VI) and (VII), and also the amines of general formula $R_3NH_2$, when their preparation method is not described, are available commercially or are described in the literature, or may be prepared according to various methods described in the literature or known to the skilled person.

The invention, according to another of its aspects, likewise provides the compounds of formula (II) and (V). These compounds are useful as intermediates in the synthesis of the compounds of formula (I).

The following examples are presented to more specifically define and set forth particular species of the invention. They are for illustrative purposes only, and should not be construed as limiting the spirit and scope of the invention as defined by the claims that follow.

The microanalyses, IR and NMR spectra and/or the LC-MS (liquid chromatography coupled to mass spectroscopy) confirm the structures and the purities of the compounds obtained.

m.p. (° C.) represents the melting point in degrees Celsius.

The numbers in parentheses in the titles of the examples correspond to those in the 1st column of the table thereafter.

EXAMPLE 1

Compound 85

2-(methylamino)-2-oxoethyl trans-4-(3-phenylprop-2-en-1-yl)piperazine-1-carboxylate

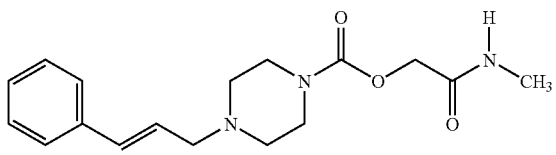

1.1. 2-(ethoxy)-2-oxoethyl trans-4-(3-phenylprop-2-en-1-yl)piperazine-1-carboxylate A solution of 1.40 g (6.93 mmol) of trans-1-cinnamylpiperazine and 1.74 g (7.76 mmol) of ethyl{[(phenoxy)carbonyl]oxy}acetate (J. Med. Chem., 1999, 42, 277-290) in 15 ml of toluene is heated at 80° C. overnight. It is evaporated to dryness and the residue is taken up in 50 ml of ethyl acetate. It is washed with 2 times 20 ml of water and 1 times 10 ml of saturated aqueous sodium chloride solution. It is dried over sodium sulphate and evaporated to dryness. The residue is purified by chromatography on silica gel, eluting with a 50/50 mixture of cyclohexane and ethyl acetate, then with ethyl acetate, to give 0.814 g of product in the form of a pale yellow oil.

1.2. 2-(methylamino)-2-oxoethyl trans-4-(3-phenylprop-2-en-1-yl)piperazine-1-carboxylate 0.8 g (2.4 mmol) of 2-(ethoxy)-2-oxoethyl trans-4-(3-phenylprop-2-en-1-yl)piperazine-1-carboxylate, obtained in step 1.1., is dissolved in 10 ml of a 2M solution of methylamine (20 mmol) in methanol. The solution is left to react for an hour and a half at ambient temperature and is then evaporated to dryness. The residue is purified by chromatography on silica gel, eluting first with ethyl acetate and then with a mixture 90/10 mixture of ethyl acetate and methanol. This gives 0.548 g of a white powder.

Melting point (° C.): 109-111 LC-MS: M+H=318 $^1$H NMR (DMSO-$d_6$): δ (ppm): 7.80 (broad s, 1H); 7.50-7.15 (m, 5H); 6.55 (d, 1H); 6.25 (td, 1H); 4.40 (s, 2H); 3.40 (m, 4H); 3.10 (d, 2H); 2.60 (d, 3H); 2.40 (m, 4H).

EXAMPLE 2

Compound 99

2-amino-2-oxoethyl 4-{3-[3-(trifluoromethyl)phenyl]prop-2-yn-1-yl}-1,4-diazepane-1-carboxylate

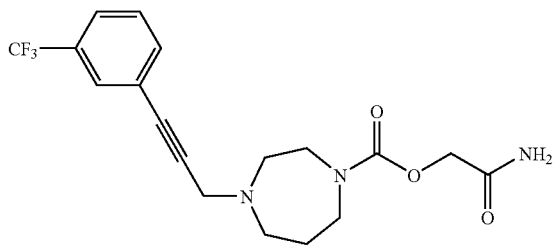

2.1. 4-{3-[3-(trifluoromethyl)phenyl]prop-2-yn-1-yl}-1,4-diazepane-1-carbaldehyde A mixture of 1.28 g (10 mmol) of 1,4-diazepane-1-carbaldehyde and 0.33 g (11 mmol) of paraformaldehyde in 13 ml of dioxane is heated at 80° C. until a homogeneous solution is obtained. 1.70 g (10 mmol) of 3-trifluoromethylphenylacetylene in solution in 7 ml of dioxane and 1.81 g (10 mmol) of copper diacetate are added. The mixture is heated at 80° C. for 4 hours. It is cooled to ambient temperature and diluted with 75 ml of ethyl acetate. The organic phase is washed with 25 ml of 30% ammonia solution and with saturated aqueous sodium chloride solution. It is dried over sodium sulphate and evaporated to dryness. The residue is purified by chromatography on silica gel, eluting with a 98/2/0.2 then 96/4/0.4 and 94/6/0.6 mixture of dichloromethane, methanol and 30% ammonia, to give 2.67 g of product in the form of a yellow oil.

2.2. 4-{3-[3-(trifluoromethyl)phenyl]prop-2-yn-1-yl}-1,4-diazepane 2.63 g (8.48 mmol) of 4-{3-[3-(trifluoromethyl)phenyl]prop-2-yn-1-yl}-1,4-diazepane-1-carbaldehyde, obtained in step 2.1., are dissolved in 7.5 ml of methanol. 3.5 ml of a 35% aqueous sodium hydroxide (30 mmol) solution are added and the mixture is heated at reflux for 3 hours. It is cooled to ambient temperature. It is diluted with 20 ml of water and 75 ml of dichloromethane. The phases are separated and then the aqueous phase is extracted with 2 times 25 ml of dichloromethane. The organic phases are washed with 25 ml of water and then with 25 ml of saturated aqueous sodium chloride solution. They are dried over sodium sulphate and evaporated to dryness, to give 2.25 g of product in the form of a red oil, which is used as it is in the following step.

2.3. 2-(ethyloxy)-2-oxoethyl 4-{3-[3-(trifluoromethyl)phenyl]prop-2-yn-1-yl}-1,4-diazepane-1-carboxylate A solution of 2.25 g (7.95 mmol) of 4-{3-[3-(trifluoromethyl)phenyl]prop-2-yn-1-yl}-1,4-diazepane, obtained in step 2.2., and 2.68 g (11.9 mmol) of ethyl {[(phenyloxy)carbonyl]oxy}acetate in 10 ml of toluene is heated at 60° C. overnight. 5 g of silica are added and the mixture is evaporated to dryness. The residue is purified by chromatography on silica gel, eluting with a 60/40 then 40/60 mixture of cyclohexane and ethyl acetate and then with ethyl acetate, to give 2.42 g of product in the form of an orange-colored oil.

2.4. 2-amino-2-oxoethyl 4-{3-[3-(trifluoromethyl)phenyl]prop-2-yn-1-yl}-1,4-diazepane-1-carboxylate 0.77 g (1.87 mmol) of 2-(ethyloxy)-2-oxoethyl 4-{3-[3-(trifluoro-methyl)phenyl]prop-2-yn-1-yl}-1,4-diazepane-1-carboxylate, obtained in step 2.3., is dissolved in 14 ml of a 7M solution of ammonia (98 mmol) in methanol. The solution is left to react at ambient temperature overnight and then 2 g of silica are added and it is evaporated to dryness. The residue is purified by chromatography on silica gel, eluting with a 97/3/0.3 then 95/5/0.5 and 93/7/0.7 mixture of dichloromethane, methanol and 30% ammonia. The eluate is subsequently recrystallized from a mixture of ethyl acetate and diisopropyl ether, to give 0.57 g of white crystals.

Melting point (° C.): 102-104 LC-MS: M+H=384 $^1$H NMR (CDCl$_3$) δ (ppm): 7.70 (s, 1H); 7.55 (m, 2H); 7.45 (d, 1H); 6.15 (broad m, 1H); 5.50 (broad m, 1H); 4.65 (s, 2H); 3.65 (m+s, 6H); 2.85 (m, 4H); 1.95 (m, 2H).

EXAMPLE 3

Compound 130

2-(methylamino)-2-oxoethyl 4-{2-[(4-chlorophenyl)oxy]ethyl}piperazine-1-carboxylate

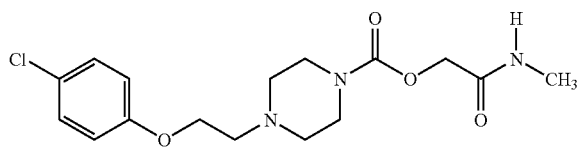

3.1. 4-nitrophenyl 2-(methylamino)-2-oxoethyl carbonate

A suspension of 2.62 g (29.4 mmol) of 2-hydroxy-N-methylacetamide and 16.5 g (58.7 mmol) of supported diisopropylethylamine (Ps-DIEA from Argonaut, loading=3.56 mmol/g) in 250 ml of dichloromethane is admixed in small portions and at ambient temperature with 5.93 g (29.4 mmol) of 4-nitrophenyl chloroformate. Orbital stirring is continued at ambient temperature for 16 hours. The resin is filtered off and rinsed with 150 ml of dichloromethane and the filtrate is concentrated under reduced pressure. This gives 6 g of product in the form or a light yellow solid, which is used as it is in the following step.

3.2. 1,1-dimethylethyl 2-(methylamino)-2-oxoethyl piperazine-1,4-dicarboxylate A solution, cooled to 0° C., of 1.1 g (3 mmol) of 4-nitrophenyl 2-(methylamino)-2-oxoethyl carbonate, prepared in step 3.1., in 10 ml of 1,2-dichloroethane is admixed dropwise at about 0° C. with a solution of 0.53 g (2.85 mmol) of 1,1-dimethylethyl piperazine-1-carboxylate in 5 ml of 1,2-dichloroethane. Stirring is continued at 0° C. for 1 hour, then at ambient temperature for 3 hours.

The mixture is concentrated under reduced pressure. The residue is purified by chromatography on silica gel, eluting with a 20/80 mixture of ethyl acetate and cyclohexane and then gradually increasing the gradient to end with elution with ethyl acetate. The eluate is triturated in diisopropyl ether, to give 0.61 g of product in the form of a white solid, which is used as it is in the following step.

3.3. 2-(methylamino)-2-oxoethyl piperazine-1-carboxylate hydrochloride

A solution of 2.68 g (8.9 mmol) of 1,1-dimethylethyl 2-(methylamino)-2-oxoethyl piperazine-1,4-dicarboxylate, obtained according to step 3.2., in 25 ml of dichloromethane is admixed with 25 ml of a 6N solution of hydrochloric acid in isopropanol. Stirring is continued at ambient temperature for 1 hour. The organic phase is separated by filtration through a hydrophobic cartridge and is concentrated under reduced pressure. Trituration in isopropanol gives 2.05 g of product.

Melting point (° C.): 167-169° C.

3.4. 2-(methylamino)-2-oxoethyl 4-{2-[(4-chlorophenyl)oxy]ethyl}piperazine-1-carboxylate A solution of 0.073 g (0.3 mmol) of 2-(methylamino)-2-oxoethyl piperazine-1-carboxylate hydrochloride, prepared in step 3.3., 0.13 g (0.9 mmol) of potassium carbonate and 0.069 g (0.29 mmol) of 1-(2-bromoethoxy)-4-chlorobenzene in 3 ml of acetonitrile is heated at 85° C. for 16 hours. After cooling to ambient temperature, the inorganic components are filtered off through a cartridge fitted with a frit and containing celite. The cartridge is rinsed with acetone and the filtrate is concentrated under reduced pressure. Chromatography on silica gel, eluting with a 95/5 mixture of dichloromethane and methanol, followed by crystallization from diisopropyl ether give 0.089 g of product in the form of a white solid.

LC-MS: M+H=356 Melting point: 159-161° C. $^1$H NMR (CDCl$_3$) δ (ppm): 7.25 (dd, 2H); 6.85 (dd, 2H); 6.05 (broad s, 1H); 4.60 (s, 2H); 4.10 (t, 2H); 3.55 (m, 4H); 2.90 (d, 3H); 2.85 (t, 2H); 2.60 (m, 4H).

EXAMPLE 4

Compound 25

2-(methylamino)-2-oxoethyl 4-(2-naphthalen-2-ylethyl)piperazine-1-carboxylate

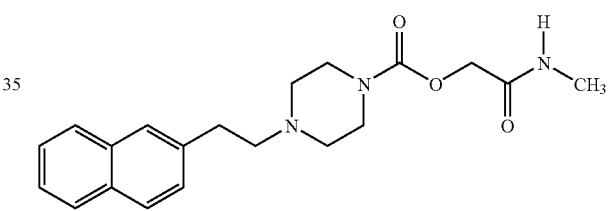

A solution, cooled to 0° C., of 0.13 g (0.75 mmol) of 2-naphthalen-2-ylethanol and 0.19 ml (1.13 mmol) of diisopropylethylamine in 7.5 ml of dichloromethane is admixed with 0.07 ml (0.9 mmol) of methanesulphonyl chloride. Stirring is continued in the cold for 0.5 hour, then at ambient temperature for 2 hours. The solution is concentrated under reduced pressure.

The residue is taken up in 5 ml of acetonitrile, and 0.12 g (0.5 mmol) of 2-(methylamino)-2-oxoethyl piperazine-1-carboxylate hydrochloride, prepared in accordance with Example 3.3., and 0.20 g (1.5 mmol) of potassium carbonate are added. The mixture is heated at 70° C. for 16 hours. After cooling to ambient temperature, it is concentrated under reduced pressure. The residue is suspended in dichloromethane and washed with saturated sodium bicarbonate solution and then with water. The organic phase is recovered by filtration on a hydrophobic membrane and is concentrated under reduced pressure. Chromatography on silica gel, eluting with a 95/5 mixture of dichloromethane and methanol, followed by crystallization from diisopropyl ether, give 0.069 g of product in the form of a white solid.

LC-MS: M+H=356 Melting point: 133-135° C. $^1$H NMR (CDCl$_3$) δ (ppm): 7.85 (m, 3H); 7.65 (s, 1H); 7.55-7.30(m, 3H); 6.05 (broad s, 1H); 4.60 (s, 2H); 3.55 (m, 4H); 3.05-2.65 (m, 7H); 2.55 (m, 4H).

EXAMPLE 5

Compound 50

2-(methylamino)-2-oxoethyl 4-(3-biphenyl-3-yl-1,1-dimethylpropyl)piperazine-1-carboxylate hydrochloride

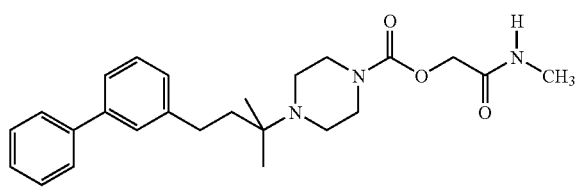

5.1. 1-(2,2-dimethylpropanoyl)-4-(1,1-dimethylprop-2-yn-1-yl)piperazine 0.756 g (6 mmol) of 1,1-dimethylprop-2-yn-1-yl acetate (J. Org. Chem. 1994, 59, 2282-4) and 2.235 g (12 mmol) of 1,1-dimethylethyl piperazine-1-carboxylate are dissolved in 9 ml of tetrahydrofuran and then 0.059 g (0.6 mmol) of cuprous chloride is added. The mixture is heated at reflux for 3 hours. After cooling to ambient temperature, 100 ml of ethyl acetate, 10 ml of 1N aqueous sodium hydroxide and 2 ml of 30% ammonia are added. The organic phase is separated off and washed with 2 times 10 ml of water and then with 10 ml of saturated aqueous sodium chloride solution. It is dried over sodium sulphate and evaporated. The product is purified by chromatography on silica gel, eluting with an 85/15 then 75/25 and 65/35 mixture of cyclohexane and ethyl acetate, to give 1.19 g (4.71 mmol) of product in the form of a pale yellow solid.

Melting point: 106-109° C.

5.2. 1-(3-biphenyl-3-yl-1,1-dimethylprop-2-yn-1-yl)-4-(2,2-dimethylpropanoyl)piperazine 1.05 g mmol) of 3g (3.6 mmol) of 1-(2,2-dimethylpropanoyl)-4-(1,1-dimethylprop-2-yn-1-yl)piperazine, prepared in step 5.1., 0.75 ml (5.38 mmol) of triethylamine and 0.028 g (0.11 mmol) of triphenylphosphine are dissolved in 8 ml of tetrahydrofuran. Under an argon atmosphere, 0.126 g (0.18 mmol) of the dichloride complex of bis(triphenylphosphine) palladium is added. The mixture is stirred for 15 minutes and then 0.014 g (0.07 mmol) of cuprous iodide is added. The mixture is stirred at ambient temperature for 4 hours and then at 60° C. overnight. After cooling to temperature it is diluted with 25 ml of ethyl acetate and filtered on paper. The solid is rinsed with 4 times 10 ml of ethyl acetate. 4 g of silica are added to the filtrate, which is evaporated to dryness. The residue is purified by chromatography on silica gel, eluting with a 90/10 then 80/20 and 70/30 mixture of cyclohexane and ethyl acetate, to give 0.90 g (2.22 mmol) of product in the form of a orange-colored oil.

5.3. 1,1-dimethylethyl 4-(3-biphenyl-3-yl-1,1-dimethylpropyl)piperazine-1-carboxylate 0.87 g (2.15 mmol) of 1-(3-biphenyl-3-yl-1,1-dimethylprop-2-yn-1-yl)-4-(2,2-dimethylpropanoyl)piperazine, prepared in step 5.2., is dissolved in a mixture of 5 ml of methanol and 15 ml of ethyl acetate. 0.2 g of platinum oxide is added and the mixture is stirred under a hydrogen atmosphere at 40 psi for 6 hours. It is filtered on paper and the filter product is rinsed with 3 times 10 ml of ethyl acetate. 2 g of silica are added to the filtrate, which is evaporated to dryness. The residue is purified by chromatography on silica gel, eluting with a 90/10 then 85/15 and 80/20 mixture of cyclohexane and ethyl acetate, to give 0.36 g (0.88 mmol) of product in the form of a colorless oil.

5.4. 1-(3-biphenyl-3-yl-1,1-dimethylpropyl)piperazine 0.65 ml (8.4 mmol) of trifluoroacetic acid is added to a solution of 0.35 g (0.86 mmol) of 1,1-dimethylethyl 4-(3-biphenyl-3-yl-1,1-dimethylpropyl)piperazine-1-carboxylate, prepared in step 5.3., in 5 ml of dichloromethane. The mixture is stirred for 2 hours and then 0.65 ml of trifluoroacetic acid is added. It is stirred for 2 more hours and then diluted with 10 ml of 1,2-dichloroethane and evaporated to dryness. The residue is taken up in a mixture of 50 ml of dichloromethane and 20 ml of 15% aqueous sodium hydroxide solution. The phases are separated and the aqueous phase is extracted with 2 times 20 ml of dichloromethane. The organic phases are washed with 10 ml of water and then with 20 ml of saturated aqueous sodium chloride solution, dried over sodium sulphate and evaporated, to give 0.25 g (0.81 mmol) of product in the form of a yellow oil.

5.5. 2-(methylamino)-2-oxoethyl 4-(3-biphenyl-3-yl-1,1-dimethylpropyl)piperazine-1-carboxylate hydrochloride A solution of 0.25 g (0.81 mmol) of 1-(3-biphenyl-3-yl-1,1-dimethylpropyl)piperazine, prepared in step 5.4., and 1.5 g (1.22 mmol) of ethyl {[(phenyloxy)carbonyl]oxy}acetate is heated at 60° C. overnight and then evaporated to dryness. The residue is dissolved in a mixture of 4 ml of a 2M methylamine (8 mmol) solution in tetrahydrofuran and 2 ml of methanol. The solution is left to react overnight and then 1 g of silica is added and the mixture is evaporated. The product is purified by chromatography on silica gel, eluting with a 98/2 then 96/4 and 94/6 mixture of dichloromethane and methanol, to give 0.23 g (0.54 mmol) of product in the form of a colourless gum.

The product is dissolved in 5 ml of ethyl acetate, and 1 ml of a 5N solution of hydrochloric acid in isopropanol is added. The mixture is evaporated to dryness. The residue is taken up in 15 ml of hot ethyl acetate. The solid is filtered off, rinsed with 2 times 3 ml of ethyl acetate and dried, to give 0.215 g (0.46 mmol) of product in the form of white powder.

LC-MS: M+H=424 Melting point: 212-216° C. (dec.) $^1$H NMR (CDCl$_3$) δ (ppm): 12.50 (broad s, 1H); 7.55 (d, 2H); 7.40 (m, 6H); 7.20 (d, 1H); 6.05 (broad s, 1H); 4.60 (s, 2H); 4.30-4.10 (m, 4H); 3.55 (broad d, 2H); 3.05-2.75 (m+d, 5H); 2.15 (m, 2H); 1.70 (s, 8H).

EXAMPLE 6

Compound 29

2-(methylamino)-2-oxoethyl 4-{2-[3-(4-chlorophenyl)isoxazol-5-yl]ethyl}piperazine-1-carboxylate

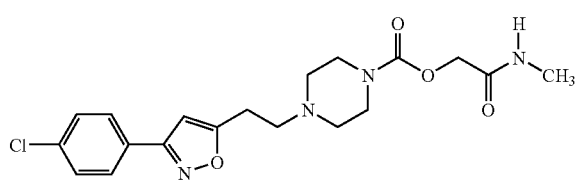

6.1. 2-[3-(4-chlorophenyl)isoxazol-5-yl]ethanol 1.63 ml (11.58 mmol) of triethylamine are added dropwise to a solution of 1.18 ml (15.57 mmol) of but-4-yn-1-ol and 2.0 g (10.52 mmol) of 4-chloro-N-hydroxybenzenecarboximidoyl chloride (J. Med. Chem. 1998, 41, 4556-66) in 30 ml of dichloromethane, cooled with an ice bath. The mixture is left to react at ambient temperature overnight. 50 ml of dichloromethane are added and the mixture is washed with 2 times 50 ml of water and then with 50 ml of saturated aqueous sodium chloride solution. After drying over sodium sulphate, the system is evaporated. The residue is purified by chromatography on silica gel, eluting with an 80/20 then 70/30 mixture of cyclohexane and ethyl acetate, to give 1.1 g (4.91 mmol) of product in the form of a white solid.

Melting point: 65-67° C.

6.2. 2-(methylamino)-2-oxoethyl 4-{2-[3-(4-chlorophenyl)isoxazol-5-yl]ethyl}piperazine-1-carboxylate A solution of 0.100 g (0.447 mmol) of 2-[3-(4-chlorophenyl)isoxazol-5-yl]ethanol, prepared in step 6.1., and 0.082 ml (0.47 mmol) of diisopropylethylamine in 5 ml of dichloromethane, is admixed with 0.036 ml (0.469 mmol) of methanesulphonyl chloride. The mixture is stirred at ambient temperature for 4 hours and then washed with saturated aqueous ammonium chloride solution and saturated aqueous sodium chloride solution. It is concentrated under reduced pressure. The residue is taken up in 5 ml of acetonitrile, and 0.107 g (0.45 mmol) of 2-(methylamino)-2-oxoethyl piperazine-1-carboxylate hydrochloride, prepared in accordance with Example 3.3., and 0.186 g (1.35 mmol) of potassium carbonate are added. The mixture is heated at 75° C. for 16 hours. After cooling to ambient temperature, it is concentrated under reduced pressure. The residue is taken up in ethyl acetate and washed with water and then with saturated aqueous sodium chloride solution. The mixture is evaporated and the residue is purified by chromatography on silica gel, eluting with dichloromethane and then with a 90/10 mixture of dichloromethane and methanol. This gives 0.054 g (0.132 mmol) of product in the form of a white solid.

LC-MS: M+H=407 Melting point: 130-132° C. $^1$H NMR (DMSO-d$_6$) δ (ppm): 7.85 (d, 2H); 7.75 (unresolved complex, 1H); 7.55 (d, 2H); 6.85 (s, 1H); 4.40 (s, 2H); 3.40 (m, 4H); 2.95 (t, 2H); 2.70 (t, 2H); 2.55 (d, 3H); 2.40 (m, 4H).

EXAMPLE 7

Compound 52

2-(methylamino)-2-oxoethyl 4-[3-(3'-chlorobiphenyl-3-yl)propyl]piperazine-1-carboxylate

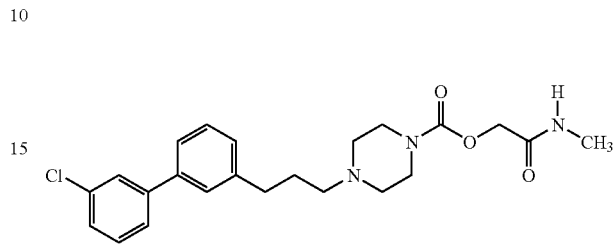

7.1. 3-(3-bromophenyl)propan-1-ol

A suspension of 1.84 g (8 mmol) of 3-(3-bromophenyl)propionic acid and 0.91 g (24 mmol) of sodium borohydride in 20 ml of THF, cooled to 0° C., is admixed in small portions with 3.2 ml (25 mmol) of trifluoroborane-diethyl ether complex. Stirring is continued in the cold for 1 hour, and then at ambient temperature for 16 hours. The reaction mixture is cooled to 0° C. and neutralized to a pH of 7~8 by adding a 1N solution of aqueous sodium hydroxide. It is concentrated under reduced pressure and then the residue is taken up in water. It is extracted with dichloromethane and dried over sodium sulphate. Following filtration, the organic phase is concentrated under reduced pressure. This gives 1.62 g (7.53 mmol) of product in the form of an oil, which is used as it is in the following step.

7.2. 2-(methylamino)-2-oxoethyl 4-[3-(3-bromophenyl)propyl]piperazine-1-carboxylate A solution of 1.57 g (6.7 mmol) of 3-(3-bromophenyl)propan-1-ol, prepared in step 7.1., and 1.73 ml (10.1 mmol) of diisopropylethylamine in 38 ml of dichloromethane, cooled to 0° C., is admixed with 0.63 ml (8.14 mmol) of methanesulphonyl chloride. Stirring is continued in the cold for 0.5 hour and then at ambient temperature for 2 hours. The mixture is concentrated under reduced pressure and then the residue is suspended in 35 ml of acetonitrile. 1.34 g (5.35 mmol) of 2-(methylamino)-2-oxoethyl piperazine-1-carboxylate hydrochloride, prepared in accordance with Example 3.3., and 2.2 g (16 mmol) of potassium carbonate are added. The mixture is heated at 75° C. for 16 hours. After cooling to ambient temperature it is concentrated under reduced pressure and then the residue is taken up in water. It is extracted with ethyl acetate and dried over sodium sulphate. Following filtration, the organic phase is concentrated under reduced pressure. It is purified by chromatography on silica gel, eluting with a 98/2 mixture of dichloromethane and methanol. Crystallization from diisopropyl ether gives 0.84 g (2.10 mmol) of white crystals.

7.3. 2-(methylamino)-2-oxoethyl 4-[3-(3'-chlorobiphenyl-3-yl)propyl]piperazine-1-carboxylate A suspension of 0.14 g (0.35 mmol) of 2-(methylamino)-2-oxoethyl 4-[3-(3-bromophenyl)propyl]piperazine-1-carboxylate, prepared in step 7.2., in a mixture of 4 ml of toluene and 0.6 ml of ethanol is admixed with 0.08 g (0.07 mol) of the tetrakis(triphenylphosphine)palladium complex, 1.05 ml (2.1 mmol) of a 2M aqueous solution of sodium carbonate and 0.22 g (1.4 mmol) of 3-chlorobenzeneboronic acid. The mixture is heated to 150° C. under microwave irradiation for 5 minutes and the organic phase is recovered by filtration on a cartridge equipped with a frit and containing celite and sodium sulphate. The cartridge is rinsed with toluene and the filtrate is concentrated under reduced pressure. The product is purified by chromatography on silica gel, eluting with a 90/10 mixture of ethyl acetate and methanol. The eluate is subsequently taken up in n-heptane, to give 0.086 g (0.18 mmol) of product in the form of white crystals.

LC-MS: M+H=430 Melting point: 82-85° C. $^1$H NMR δ (ppm): 7.35 (m, 8H); 6.05 (broad s, 1H); 4.6 (s, 2H); 3.55 (m, 4H); 2.85 (d, 3H); 2.75 (t, 2H); 2.45 (m, 6H); 1.9 (m, 2H).

Table 1 below illustrates the chemical structures and the physical properties of some compounds according to the invention. In the "base or salt" column, "base" represents a compound in the form of the free base, whereas "HCl" represents a compound in hydrochloride form.

TABLE 1

(I)

| Cpd | $R_1$ | G | $[A]_p$ | n | $R_2$ | $R_3$ | m.p. (° C.) (or M + H) | base or salt |
|---|---|---|---|---|---|---|---|---|
| 1. | 2-F-phenyl | bond | $CH_2$ | 1 | H | $CH_3$ | 196-200 | HCl |
| 2. | 2-Cl-phenyl | bond | $CH_2$ | 1 | H | $CH_3$ | 212-217 | HCl |
| 3. | 3-F-phenyl | bond | $CH_2$ | 1 | H | $CH_3$ | 161-166 | HCl |
| 4. | 3-I-phenyl | bond | $CH_2$ | 1 | H | $CH_3$ | (418) | base |
| 5. | 3-Cl-phenyl | bond | $CH_2$ | 1 | H | $CH_3$ | 203-207 | HCl |
| 6. | 4-Cl-phenyl | bond | $CH_2$ | 1 | H | $CH_3$ | 112-115 | HCl |
| 7. | 4-$CH_3$O-phenyl | bond | $CH_2$ | 1 | H | $CH_3$ | 155-159 | HCl |
| 8. | 4-(phenyl$CH_2$O)-phenyl | bond | $CH_2$ | 1 | H | $CH_3$ | 172-178 | HCl |
| 9. | 4-$(CH_3)_2$CH-phenyl | bond | $CH_2$ | 1 | H | $CH_3$ | 104-108 | HCl |
| 10. | 3-phenyl-phenyl | bond | $CH_2$ | 1 | H | $CH_3$ | 111-114 | HCl |
| 11. | 4-phenyl-phenyl | bond | $CH_2$ | 1 | H | $CH_3$ | 173-179 | HCl |
| 12. | naphthalen-1-yl | bond | $CH_2$ | 1 | H | $CH_3$ | 143-145 | base |
| 13. | naphthalen-2-yl | bond | $CH_2$ | 1 | H | $CH_3$ | 184-186 | HCl |
| 14. | phenyl | bond | $(CH_2)_2$ | 1 | H | $CH_3$ | 167-169 | base |
| 15. | 3-Br-phenyl | bond | $(CH_2)_2$ | 1 | H | $CH_3$ | (384) | base |
| 16. | 4-Br-phenyl | bond | $(CH_2)_2$ | 1 | H | $CH_3$ | (384) | base |
| 17. | 4-$CH_3$O-phenyl | bond | $(CH_2)_2$ | 1 | H | $CH_3$ | 124-126 | base |
| 18. | 3-phenyl-phenyl | bond | $(CH_2)_2$ | 1 | H | $CH_3$ | 118-120 | base |
| 19. | 4-phenyl-phenyl | bond | $(CH_2)_2$ | 1 | H | $CH_3$ | 148-150 | base |
| 20. | naphthalen-1-yl | bond | $(CH_2)_2$ | 1 | H | H | 125-127 | base |
| 21. | naphthalen-1-yl | bond | $(CH_2)_2$ | 1 | H | $CH_3$ | 109-112 | base |
| 22. | naphthalen-1-yl | bond | $(CH_2)_2$ | 1 | H | $CH_2CH_3$ | 113-115 | base |
| 23. | naphthalen-1-yl | bond | $(CH_2)_2$ | 1 | H | cyclopropyl | 125-127 | base |
| 24. | naphthalen-1-yl | bond | $(CH_2)_2$ | 1 | H | $CH_2$-cyclopropyl | 113-115 | base |
| 25. | naphthalen-2-yl | bond | $(CH_2)_2$ | 1 | H | $CH_3$ | 133-135 | base |
| 26. | naphthalen-2-yl | bond | $(CH_2)_2$ | 2 | H | H | 115-119 | base |
| 27. | indol-3-yl | bond | $(CH_2)_2$ | 1 | H | $CH_3$ | 121-123 | base |
| 28. | 3-(4-Cl-phenyl)-1H-methyl-pyrazol-5-yl | bond | $(CH_2)_2$ | 1 | H | $CH_3$ | 141-143 | base |
| 29. | 3-(4-Cl-phenyl)isoxazol-5-yl | bond | $(CH_2)_2$ | 1 | H | $CH_3$ | 130-132 | base |
| 30. | 5-(4-Cl-phenyl)isoxazol-3-yl | bond | $(CH_2)_2$ | 1 | H | $CH_3$ | 146-148 | base |
| 31. | 6-(4-Cl-phenyl)pyrimidin-4-yl | bond | $(CH_2)_2$ | 1 | H | $CH_3$ | 132-134 | base |
| 32. | 1,1-diphenylmethyl | bond | $(CH_2)_2$ | 1 | H | $CH_3$ | 86-88 | base |
| 33. | phenyl | bond | $(CH_2)_3$ | 1 | H | $CH_3$ | 315-317 | HCl |
| 34. | 3-Cl-phenyl | bond | $(CH_2)_3$ | 1 | H | $CH_3$ | 85-87 | base |
| 35. | 4-Cl-phenyl | bond | $(CH_2)_3$ | 1 | H | $CH_3$ | 115-117 | base |

TABLE 1-continued (I)

| Cpd | R₁ | G | [A]ₚ | n | R₂ | R₃ | m.p. (° C.) (or M + H) | base or salt |
|---|---|---|---|---|---|---|---|---|
| 36. | 3-Br-phenyl | bond | (CH₂)₃ | 1 | H | CH₃ | (398) | base |
| 37. | 4-Br-phenyl | bond | (CH₂)₃ | 1 | H | CH₃ | (398) | base |
| 38. | 3-CN-phenyl | bond | (CH₂)₃ | 1 | H | CH₃ | 107-109 | base |
| 39. | 3-CF₃-phenyl | bond | (CH₂)₃ | 1 | H | CH₃ | 98-100 | base |
| 40. | 4-CF₃-phenyl | bond | (CH₂)₃ | 1 | H | CH₃ | 85-87 | base |
| 41. | 2-Cl,4-Cl-phenyl | bond | (CH₂)₃ | 1 | H | CH₃ | 103-105 | base |
| 42. | 2-Cl,5-Cl-phenyl | bond | (CH₂)₃ | 1 | H | H | 128-130 | base |
| 43. | 2-Cl,5-Cl-phenyl | bond | (CH₂)₃ | 1 | H | CH₃ | 121-123 | base |
| 44. | pyrimidin-2-yl | bond | (CH₂)₃ | 1 | H | CH₃ | 103-105 | base |
| 45. | pyrimidin-5-yl | bond | (CH₂)₃ | 1 | H | CH₃ | 116-118 | base |
| 46. | thiazol-2-yl | bond | (CH₂)₃ | 1 | H | CH₃ | 83-85 | base |
| 47. | 2-phenyl-phenyl | bond | (CH₂)₃ | 1 | H | CH₃ | (396) | base |
| 48. | 3-phenyl-phenyl | bond | (CH₂)₃ | 1 | H | CH₃ | 99-101 | base |
| 49. | 4-phenyl-phenyl | bond | (CH₂)₃ | 1 | H | CH₃ | 110-113 | base |
| 50. | 3-phenyl-phenyl | bond | (CH₂)₂—C(CH₃)₂ | 1 | H | CH₃ | 212-216 | HCl |
| 51. | 4-phenyl-phenyl | bond | (CH₂)₂—C(CH₃)₂ | 1 | H | CH₃ | 101-103 | base |
| 52. | 3-(3-Cl-phenyl)-phenyl | bond | (CH₂)₃ | 1 | H | CH₃ | 82-85 | base |
| 53. | 3-(4-Cl-phenyl)-phenyl | bond | (CH₂)₃ | 1 | H | CH₃ | 136-138 | base |
| 54. | 3-(3-CH₃O)phenyl)-phenyl | bond | (CH₂)₃ | 1 | H | CH₃ | (426) | base |
| 55. | 3-(4-CH₃O)phenyl)-phenyl | bond | (CH₂)₃ | 1 | H | CH₃ | 135-137 | base |
| 56. | 3-(3-CN-phenyl)-phenyl | bond | (CH₂)₃ | 1 | H | CH₃ | 152-154 | base |
| 57. | 3-(4-CN-phenyl)-phenyl | bond | (CH₂)₃ | 1 | H | CH₃ | 137-139 | base |
| 58. | 4-(3-Cl-phenyl)-phenyl | bond | (CH₂)₃ | 1 | H | CH₃ | 101-103 | base |
| 59. | 4-(4-Cl-phenyl)-phenyl | bond | (CH₂)₃ | 1 | H | CH₃ | 125-128 | base |
| 60. | 4-(3-CH₃O)phenyl)-phenyl | bond | (CH₂)₃ | 1 | H | CH₃ | 97-100 | base |
| 61. | 4-(4-CH₃O)phenyl)-phenyl | bond | (CH₂)₃ | 1 | H | CH₃ | 128-130 | base |
| 62. | 4-(3-CN-phenyl)-phenyl | bond | (CH₂)₃ | 1 | H | CH₃ | 108-110 | base |
| 63. | 4-(4-CN-phenyl)-phenyl | bond | (CH₂)₃ | 1 | H | CH₃ | 148-150 | base |
| 64. | naphthalen-1-yl | bond | (CH₂)₃ | 1 | H | CH₃ | 104-106 | HCl |
| 65. | naphthalen-2-yl | bond | (CH₂)₃ | 1 | H | CH₃ | 110-112 | base |
| 66. | 3-(4-Cl-phenyl)-1H-methyl-pyrazol-5-yl | bond | (CH₂)₃ | 1 | H | CH₃ | 157-159 | base |
| 67. | 5-(4-Cl-phenyl)isoxazol-3-yl | bond | (CH₂)₃ | 1 | H | CH₃ | 125-127 | base |
| 68. | 3-(4-Cl-phenyl)isoxazol-5-yl | bond | (CH₂)₃ | 1 | H | H | 132-134 | base |
| 69. | 3-(4-Cl-phenyl)isoxazol-5-yl | bond | (CH₂)₃ | 1 | H | CH₃ | 108-110 | base |

TABLE 1-continued (I)

| Cpd | R₁ | G | [A]ₚ | n | R₂ | R₃ | m.p. (° C.) (or M + H) | base or salt |
|---|---|---|---|---|---|---|---|---|
| 70. | 3-(naphthalen-2-yl)isoxazol-5-yl | bond | (CH₂)₃ | 1 | H | CH₃ | 71-73 | base |
| 71. | 1,1-di-(4-F-phenyl)methyl | bond | (CH₂)₃ | 1 | H | CH₃ | (446) | base |
| 72. | 3-Cl-phenyl | bond | (CH₂)₄ | 1 | H | CH₃ | 103-105 | base |
| 73. | 4-Cl-phenyl | bond | (CH₂)₄ | 1 | H | CH₃ | 120-122 | base |
| 74. | 3-CN-phenyl | bond | (CH₂)₄ | 1 | H | CH₃ | 127-129 | base |
| 75. | 3-CF₃-phenyl | bond | (CH₂)₄ | 1 | H | CH₃ | 98-100 | base |
| 76. | 4-CF₃-phenyl | bond | (CH₂)₄ | 1 | H | CH₃ | 129-131 | base |
| 77. | pyrimidin-2-yl | bond | (CH₂)₄ | 1 | H | CH₃ | 141-143 | base |
| 78. | pyrimidin-5-yl | bond | (CH₂)₄ | 1 | H | CH₃ | 114-116 | base |
| 79. | thiazol-2-yl | bond | (CH₂)₄ | 1 | H | CH₃ | 93-95 | base |
| 80. | naphthalen-1-yl | bond | (CH₂)₄ | 1 | H | CH₃ | 90-92 | base |
| 81. | naphthalen-2-yl | bond | (CH₂)₄ | 1 | H | CH₃ | 109-111 | base |
| 82. | 2-phenyl-phenyl | bond | (CH₂)₄ | 1 | H | CH₃ | 92-94 | base |
| 83. | 3-phenyl-phenyl | bond | (CH₂)₄ | 1 | H | CH₃ | 97-99 | base |
| 84. | phenyl | bond | CH=CHCH₂ (E) | 1 | H | H | 115-117 | base |
| 85. | phenyl | bond | CH=CHCH₂ (E) | 1 | H | CH₃ | 109-111 | base |
| 86. | 3-Cl-phenyl | bond | C≡CCH₂ | 1 | H | CH₃ | 114-116 | base |
| 87. | 4-Cl-phenyl | bond | C≡CCH₂ | 1 | H | CH₃ | 127-129 | base |
| 88. | 3-CF₃-phenyl | bond | C≡CCH₂ | 1 | H | CH₃ | 131-133 | base |
| 89. | 4-CF₃-phenyl | bond | C≡CCH₂ | 1 | H | CH₃ | 125-127 | base |
| 90. | 3-CH-phenyl | bond | C≡CCH₂ | 1 | H | CH₃ | 134-140 | base |
| 91. | pyrimidin-2-yl | bond | C≡CCH₂ | 1 | H | CH₃ | 137-139 | base |
| 92. | pyrimidin-5-yl | bond | C≡CCH₂ | 1 | H | CH₃ | 151-153 | base |
| 93. | thiazol-2-yl | bond | C≡CCH₂ | 1 | H | CH₃ | 111-113 | base |
| 94. | naphthalen-1-yl | bond | C≡CCH₂ | 1 | H | CH₃ | 131-134 | base |
| 95. | naphthalen-2-yl | bond | C≡CCH₂ | 1 | H | CH₃ | (366) | base |
| 96. | 2-phenyl-phenyl | bond | C≡CCH₂ | 1 | H | CH₃ | (392) | base |
| 97. | 3-phenyl-phenyl | bond | C≡CCH₂ | 1 | H | CH₃ | 125-127 | base |
| 98. | 4-phenyl-phenyl | bond | C≡CC(CH₃)₂ | 1 | H | CH₃ | 137-139 | base |
| 99. | 3-CF₃-phenyl | bond | C≡CCH₂ | 2 | H | H | 102-104 | base |
| 100. | 3-CF₃-phenyl | bond | C≡CCH₂ | 2 | H | CH₃ | 92-94 | base |
| 101. | 3-Cl-phenyl | bond | C≡C(CH₂)₂ | 1 | H | CH₃ | 115-117 | base |
| 102. | 4-CT-phenyl | bond | C≡C(CH₂)₂ | 1 | H | CH₃ | 141-143 | base |
| 103. | 3-CF₃-phenyl | bond | C≡C(CH₂)₂ | 1 | H | CH₃ | 93-95 | base |
| 104. | 4-CF₃-phenyl | bond | C≡C (CH₂)₂ | 1 | H | CH₃ | 142-144 | base |
| 105. | 3-CN-phenyl | bond | C≡C(CH₂)₂ | 1 | H | CH₃ | 144-146 | base |
| 106. | pyrimidin-2-yl | bond | C≡C(CH₂)₂ | 1 | H | CH₃ | 120-122 | base |
| 107. | pyrimidin-5-yl | bond | C≡C(CH₂)₂ | 1 | H | CH₃ | 159-161 | base |
| 108. | thiazol-2-yl | bond | C≡C(CH₂)₂ | 1 | H | CH₃ | 103-105 | base |
| 109. | naphthalen-1-yl | bond | C≡C(CH₂)₂ | 1 | H | CH₃ | 99-101 | base |
| 110. | naphthalen-2-yl | bond | C≡C(CH₂)₂ | 1 | H | CH₃ | 140-142 | base |
| 111. | 2-phenyl-phenyl | bond | C≡C(CH₂)₂ | 1 | H | CH₃ | (406) | base |
| 112. | 3-phenyl-phenyl | bond | C≡C(CH₂)₂ | 1 | H | CH₃ | 102-104 | base |
| 113. | 3-Cl-phenyl | bond | C≡C(CH₂)₃ | 1 | H | CH₃ | 79-81 | base |
| 114. | 4-Cl-phenyl | bond | C≡C(CH₂)₃ | 1 | H | CH₃ | 126-128 | base |
| 115. | 2-F,4-Cl-phenyl | bond | C≡C(CH₂)₃ | 1 | H | CH₃ | 131-133 | base |
| 116. | 2-Cl,4-F-phenyl | bond | C≡C(CH₂)₃ | 1 | H | CH₃ | 133-135 | base |
| 117. | 2-Cl,4-Cl-phenyl | bond | C≡C(CH₂)₃ | 1 | H | CH₃ | 133-135 | base |
| 118. | 2-Cl,5-Cl-phenyl | bond | C≡C(CH₂)₃ | 1 | H | CH₃ | 110-112 | base |
| 119. | 3-Cl,4-Cl-phenyl | bond | C≡C(CH₂)₃ | 1 | H | CH₃ | 119-121 | base |
| 120. | 3-Cl,4-F-phenyl | bond | C≡C(CH₂)₃ | 1 | H | CH₃ | 98-100 | base |
| 121. | phenyl | O | (CH₂)₂ | 1 | H | CH₃ | 233-235 | base |
| 122. | 2-Cl-phenyl | O | (CH₂)₂ | 1 | H | H | 90-92 | base |
| 123. | 2-Cl-phenyl | O | (CH₂)₂ | 1 | H | CH₃ | 184-186 | HCl |
| 124. | 2-CN-phenyl | O | (CH₂)₂ | 1 | H | CH₃ | 109-111 | base |
| 125. | 3-Cl-phenyl | O | (CH₂)₂ | 1 | H | H | >300 | HCl |

TABLE 1-continued (I)

| Cpd | R₁ | G | [A]ₚ | n | R₂ | R₃ | m.p. (° C.) (or M + H) | base or salt |
|---|---|---|---|---|---|---|---|---|
| 126. | 3-Cl-phenyl | O | (CH₂)₂ | 1 | H | CH₃ | 105-107 | base |
| 127. | 3-CN-phenyl | O | (CH₂)₂ | 1 | H | CH₃ | 141-143 | base |
| 128. | 4-F-phenyl | O | (CH₂)₂ | 1 | H | CH₃ | 134-136 | base |
| 129. | 4-Cl-phenyl | O | (CH₂)₂ | 1 | H | H | 115-117 | base |
| 130. | 4-Cl-phenyl | O | (CH₂)₂ | 1 | H | CH₃ | 159-161 | base |
| 131. | 4-CN-phenyl | O | (CH₂)₂ | 1 | H | H | 145-147 | base |
| 132. | 4-CN-phenyl | O | (CH₂)₂ | 1 | H | CH₃ | 138-140 | base |
| 133. | 4-(CH₃)₃C-phenyl | O | (CH₂)₂ | 1 | H | CH₃ | 111-113 | HCl |
| 134. | 4-CF₃O-phenyl | O | (CH₂)₂ | 1 | H | H | 104-106 | base |
| 135. | 4-CF₃O-phenyl | O | (CH₂)₂ | 1 | H | H | 96-98 | base |
| 136. | 4-CF₃O-phenyl | O | (CH₂)₂ | 1 | H | CH₃ | 93-96 | base |
| 137. | 2-Cl,3-Cl-phenyl | O | (CH₂)₂ | 1 | H | H | 136-138 | base |
| 138. | 2-Cl,3-Cl-phenyl | O | (CH₂)₂ | 1 | H | CH₃ | 132-134 | base |
| 139. | 2-Cl,4-Cl-phenyl | O | (CH₂)₂ | 1 | H | H | 178-180 | base |
| 140. | 2-Cl,4-Cl-phenyl | O | (CH₂)₂ | 1 | H | CH₃ | 102-104 | base |
| 141. | 3-Cl,4-Cl-phenyl | O | (CH₂)₂ | 1 | H | CH₃ | 128-130 | base |
| 142. | 3-Cl,4-Cl-phenyl | O | (CH₂)₂ | 1 | H | H | 126-128 | base |
| 143. | 3-Cl,5-Cl-phenyl | O | (CH₂)₂ | 1 | H | CH₃ | 111-113 | base |
| 144. | 3-CF₃,5-CF₃-phenyl | O | (CH₂)₂ | 1 | H | CH₃ | 137-139 | base |
| 145. | 3,4-(OCH₂O)-phenyl | O | (CH₂)₂ | 1 | H | CH₃ | 139-141 | base |
| 146. | 3-phenyl-phenyl | O | (CH₂)₂ | 1 | H | H | 120-122 | HCl |
| 147. | 3-phenyl-phenyl | O | (CH₂)₂ | 1 | H | CH₃ | 143-145 | HCl |
| 148. | 4-phenyl-phenyl | O | (CH₂)₂ | 1 | H | H | 238-240 | base |
| 149. | 4-phenyl-phenyl | O | (CH₂)₂ | 1 | H | CH₃ | 130-132 | base |
| 150. | naphthalen-1-yl | O | (CH₂)₂ | 1 | H | H | 116-118 | base |
| 151. | naphthalen-1-yl | O | (CH₂)₂ | 1 | H | CH₃ | 135-137 | base |
| 152. | naphthalen-2-yl | O | (CH₂)₂ | 1 | H | H | 88-90 | base |
| 153. | naphthalen-2-yl | O | (CH₂)₂ | 1 | H | CH₃ | 118-120 | base |
| 154. | quinolin-6-yl | O | (CH₂)₂ | 1 | H | H | 203-205 | base |
| 155. | quinolin-6-yl | O | (CH₂)₂ | 1 | H | CH₃ | 126-128 | base |
| 156. | quinolin-8-yl | O | (CH₂)₂ | 1 | H | CH₃ | 99-101 | base |
| 157. | phenyl | O | (CH₂)₃ | 1 | H | CH₃ | 103-105 | base |
| 158. | 2-Cl-phenyl | O | (CH₂)₃ | 1 | H | CH₃ | 119-121 | base |
| 159. | 3-Cl-phenyl | O | (CH₂)₃ | 1 | H | CH₃ | 95-97 | base |
| 160. | 4-Cl-phenyl | O | (CH₂)₃ | 1 | H | CH₃ | 116-118 | base |
| 161. | 2-Cl,3-Cl-phenyl | O | (CH₂)₃ | 1 | H | CH₃ | 110-112 | base |
| 162. | 2-Cl,4-Cl-phenyl | O | (CH₂)₃ | 1 | H | CH₃ | 115-117 | base |
| 163. | 2-Cl,5-Cl-phenyl | O | (CH₂)₃ | 1 | H | CH₃ | 134-136 | base |
| 164. | 2-Cl,6-Cl-phenyl | O | (CH₂)₃ | 1 | H | CH₃ | 100-102 | base |
| 165. | 3-Cl,5-Cl-phenyl | O | (CH₂)₃ | 1 | H | CH₃ | 121-123 | base |
| 166. | phenyl | C=O | (CH₂)₂ | 1 | H | CH₃ | 141-143 | base |
| 167. | 4-Cl-phenyl | C=O | (CH₂)₂ | 1 | H | CH₃ | 172-174 | base |
| 168. | phenyl | C=O | (CH₂)₃ | 1 | H | CH₃ | 110-112 | base |

The compounds of the invention were subjected to pharmacological tests permitting determination of their inhibitory effect on the enzyme FAAH (fatty acid amide hydrolase).

The inhibitory activity was demonstrated in a radio-enzymatic assay based on measuring the product of hydrolysis ([1-$^3$H] ethanolamine) of anandamide [1-$^3$H ethanolamine] by FAAH (*Life Sciences* (1995), 56, 1999-2005 and *Journal of Pharmacology and Experimental Therapeutics* (1997), 283, 729-34). Accordingly, mouse brains (minus the cerebellum) are removed and stored at −80° C. Membrane homogenates are prepared at the time of use by homogenizing the tissues in a Polytron in a 10 mM Tris-HCl buffer (pH 8) containing 150 mM NaCl and 1 mM EDTA. The enzyme reaction is subsequently conducted in 70 μl of buffer containing bovine serum albumin without fatty acids (1 mg/ml). In succession, the test compounds, at various concentrations, anandamide [1-$^3$H ethanolamine] (specific activity: 15-20 Ci/mmol) diluted to 10 μM with cold anandamide, and the membrane preparation (400 μg of frozen tissue per assay) are added. After 15 minutes at 25° C. the enzyme reaction is terminated by adding 140 μl of chloroform/methanol (2:1). The mixture is stirred for 10 minutes and then centrifuged for 15 minutes at 3500 g. An aliquot (30 μl) of the aqueous phase containing the 1-$^3$H ethanolamine is counted by liquid scintillation.

Under these conditions, the most active compounds of the invention exhibit $IC_{50}$ values (concentration inhibiting by 50% the control enzyme activity of FAAH) of between 0.001 and 1 μM.

Table 2 below shows the $IC_{50}$ of some compounds according to the invention

TABLE 2

| Compound | $IC_{50}$ |
|---|---|
| 21 | 0.072 μM |
| 48 | 0.050 μM |
| 49 | 0.032 μM |

It is therefore apparent that the compounds according to the invention have an inhibitory effect on the FAAH enzyme.

The in vivo activity of the compounds of the invention was evaluated in an analgesia test.

Accordingly, intraperitoneal (i.p.) administration of PBQ (phenylbenzoquinone, 2 mg/kg in a 0.9% sodium chloride solution containing 5% of ethanol) to male OFI mice weighing 25 to 30 g causes abdominal stretches, on average 30 twists or contractions during the period from 5 to 15 minutes after injection. The test compounds are administered orally (p.o.) or intraperitoneally (i.p.) in suspension in Tween 80 at 0.5%, 60 minutes or 120 minutes before the administration of PBQ. Under these conditions the most potent compounds of the invention reduce by 35 to 70% the number of stretches induced by PBQ, within a dose range of between 1 and 30 mg/kg. For example, compounds 49 and 69 of the table reduce by 43% and 47% respectively, the number of stretches induced by PBQ, at a dose of 10 mg/kg at 120 minutes.

The FAAH enzyme (*Chemistry and Physics of Lipids,* (2000), 108, 107-21) catalyses the hydrolysis of endogenous derivatives of amides and of esters of various fatty acids such as N-arachidonylethanolamine (anandamide), N-palmitoylethanolamine, N-oleoylethanolamine, oleamide or 2-arachidonoylglycerol. These derivatives exert various pharmacological activities by interacting, inter alia, with cannabinoid and vanilloid receptors.

The compounds of the invention block this degradation pathway and increase the tissue level of these endogenous substances. They can be used in this respect in the prevention and treatment of pathologies in which endogenous cannabinoids and/or any other substrates metabolized by the FAAH enzyme are involved. The use of compounds according to the invention in base, salt, hydrate or pharmaceutically acceptable solvate form for preparing a medicinal product intended for treating the above-mentioned pathologies forms an integral part of the invention.

The invention likewise provides medicinal compositions which comprise a compound of formula (I), or an acid addition salt or hydrate or a pharmaceutically acceptable solvate of the compound of formula (I). These medicinal products are employed in therapy, particularly in the treatment of the above-mentioned pathologies.

In accordance with another of its aspects, the present invention provides pharmaceutical compositions comprising as the active principle at least one compound according to the invention. These pharmaceutical compositions include an effective dose of a compound according to the invention, or an acid addition salt or a hydrate or pharmaceutically acceptable solvate of the said compound, and optionally one or more pharmaceutically acceptable excipients.

The said excipients are selected, according to the pharmaceutical form and the desired mode of administration, from the customary excipients, which are known to the skilled person, such as carbohydrates, cellulose and cellulose derivatives, starches, synthetic and natural polymers, sugars and sugar alcohols, gelatin, lipids, fats, lubricants and mixtures thereof.

In the pharmaceutical compositions of the present invention may be formulated for oral, sublingual, subcutaneous, intramuscular, intravenous, topical, local, intrathecal, intranasal, transdermal, pulmonary, ocular or rectal administration. When so formulated, the active principle of formula (I) above, or its acid addition salt, solvate or hydrate where appropriate, may be administered in single-dose administration form, in a mixture with conventional pharmaceutical excipients, to animals and to humans for the prophylaxis or treatment of the above disorders or diseases.

The unit-dose administration forms which are appropriate include oral forms such as tablets, soft or hard gelatin capsules, powders, granules, chewing gums and oral solutions or suspensions, forms for sublingual, buccal, intra-tracheal, intra-ocular and intra-nasal administration and for administration by inhalation, forms for subcutaneous, intramuscular or intravenous administration and forms for rectal or vaginal administration. For topical application the compounds according to the invention may be used in creams, ointments or lotions.

By way of example a single-dose administration form of a compound according to the invention in tablet form may comprise the following components:

| | |
|---|---|
| Active Compound | 50.0 mg |
| Mannitol | 223.75 mg |
| Croscaramellose sodium | 6.0 mg |
| Maize starch | 15.0 mg |
| Hydroxypropyl-methylcellulose | 2.25 mg |
| Magnesium stearate | 3.0 mg |

The single-dose forms contain a dose permitting daily administration of from 0.01 to 20 mg of active principle per kg of bodyweight, depending on the pharmaceutical form.

There may be particular cases in which higher or lower dosages are appropriate; such dosages also belong to the invention. In accordance with common practice the dosage appropriate to each patient is determined by the doctor according to the method of administration, the weight and the response of the patient.

According to another of its aspects the invention also provides a method of treating the pathologies indicated above, which comprises administering an effective dose of a compound according to the invention, one of its addition salts with a pharmaceutically acceptable acid, or a solvate or a hydrate of the said compound.

What is claimed is:

1. A compound of the formula (I)

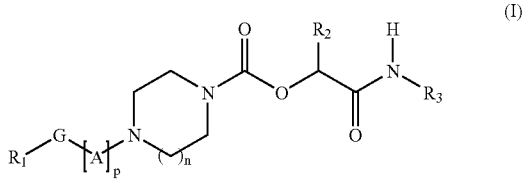

in which
n represents an integer 1 or 2;
p represents an integer ranging from 1 to 7;
A is selected from one or more groups X, Y and/or Z;
X represents a methylene group optionally substituted by one or two $C_{1-6}$-alkyl, $C_{3-7}$-cycloalkyl or $C_{3-7}$-cycloalkyl-$C_{1-3}$-alkylene groups;
Y represents either a $C_2$-alkenylene group optionally substituted by one or two $C_{1-6}$-alkyl, $C_{3-7}$-cycloalkyl or $C_{3-7}$-cycloalkyl-$C_{1-3}$-alkylene groups; or a $C_2$-alkynylene group;
Z represents a group of formula:

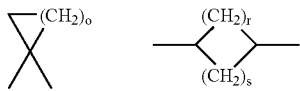

o represents an integer ranging from 1 to 5;
r and s represent integers and are defined such that r+s is a number ranging from 1 to 5;
G represents a single bond, an oxygen or sulphur atom or an SO, $SO_2$, C=O or CH(OH) group;
$R_1$ represents a group $R_4$ optionally substituted by one or more groups $R_5$ and/or $R_6$;
$R_4$ represents a group selected from a phenyl, pyridinyl, pyrimidinyl, pyridazinyl, pyrazinyl, triazinyl, pyrrolyl, furanyl, thienyl, imidazolyl, oxazolyl, thiazolyl, pyrazolyl, isoxazolyl, isothiazolyl, oxadiazolyl, thiadiazolyl, triazolyl, tetrazolyl, naphthalenyl, diphenylmethyl, quinolinyl, tetrahydroquinolinyl, isoquinolinyl, tetrahydroisoquinolinyl, quinazolinyl, quinoxalinyl, phthalazinyl, cinnolinyl, naphthyridinyl, benzofuranyl, dihydrobenzofuranyl, benzothienyl, dihydrobenzothienyl, indolyl, indolinyl, indanyl, indazolyl, isoindolyl, benzimidazolyl, benzoxazolyl, benzisoxazolyl, benzothiazolyl, benzisothiazolyl, benzotriazolyl, benzoxadiazolyl, benzothiadiazolyl, pyrrolopyridinyl, furopyridinyl, thienopyridinyl, imidazolopyridinyl, oxazolopyridinyl, thiazolopyridinyl, pyrazolopyridinyl, isoxazolopyridinyl and isothiazolopyridinyl;

$R_5$ represents a halogen atom or a cyano, nitro, $C_{1-6}$-alkyl, $C_{1-6}$-alkoxy, hydroxyl, $C_{1-6}$-thioalkyl, $C_{1-6}$-fluoroalkyl, $C_{1-6}$-fluoroalkoxy or $C_1$-$C_6$-fluorothioalkyl group, a group $NR_7R_8$, $NR_7COR_8$, $NR_7CO_2R_8$, $NR_7SO_2R_8$, $COR_7$, $CO_2R_7$, $CONR_7R_8$, $SO_2R_7$ or $SO_2NR_7R_8$, or an —O—($C_{1-3}$-alkylene)-O group;
$R_6$ represents a phenyl, phenyloxy, benzyloxy, naphthalenyl, pyridinyl, pyrimidinyl, pyridazinyl or pyrazinyl group, the group or groups $R_6$ being optionally substituted by one or more groups $R_5$ identical to or different from one another;
$R_7$ and $R_8$ represent independently of one another a hydrogen atom or a $C_{1-6}$-alkyl group, or form with the atom or atoms which carry them a ring selected from azetidine, pyrrolidine, piperidine, morpholine, thiomorpholine, azepine and piperazine, this ring being optionally substituted by a $C_{1-6}$-alkyl or benzyl group;
$R_2$ represents a hydrogen atom or a $C_{1-6}$-alkyl group;
$R_3$ represents a hydrogen atom or a $C_{1-6}$-alkyl, $C_{3-7}$-cycloalkyl or $C_{3-7}$-cycloalkyl-$C_{1-3}$-alkyl group;
in the form of a base, addition salt with an acid or hydrate.

2. The compound of formula (I) as recited in claim 1, wherein:
n represents an integer 1 or 2;
p represents an integer ranging from 1 to 7;
A is selected from one or more groups X and/or Y;
X represents a methylene group optionally substituted by one or two $C_{1-6}$-alkyl groups;
Y represents either a $C_2$-alkenylene group or a $C_2$-alkynylene group;
G represents a single bond, an oxygen atom or a C=O group;
$R_1$ represents a group $R_4$ optionally substituted by one or more groups $R_5$ and/or $R_6$;
$R_4$ represents a group selected from a phenyl, naphthalenyl, diphenylmethyl, quinolinyl, indolyl, pyrazolyl, isoxazolyl, pyrimidinyl and thiazolyl;
$R_5$ represents a halogen atom or a cyano group, a $C_{1-6}$-alkyl group, a $C_{1-6}$-alkoxy group, a $C_{1-6}$-fluoroalkyl group, a $C_1$-$C_6$-fluoroalkoxy group, or an —O—($C_{1-3}$-alkylene)-O group;
$R_6$ represents a phenyl, naphthalenyl or benzyloxy group;
$R_2$ represents a hydrogen atom or a $C_{1-6}$-alkyl group;
$R_3$ represents a hydrogen atom or a $C_{1-6}$-alkyl, $C_{3-7}$-cycloalkyl or $C_{3-7}$-cycloalkyl -$C_{1-3}$-alkyl group;
in the form of a base, addition salt with an acid or hydrate.

3. The compound of formula (I) as recited in claim 2 wherein:
n represents an integer 1 or 2;
p represents an integer ranging from 1 to 4;
A is selected from one or more groups X and/or Y;
X represents a methylene group optionally substituted by one or two $C_{1-6}$-alkyl groups;
Y represents a $C_2$-alkynylene group;
G represents a single bond or an oxygen atom;
$R_1$ represents a group $R_4$ optionally substituted by one or more groups $R_5$ and/or $R_6$;
$R_4$ represents a group selected from a phenyl, naphthalenyl or isoxazolyl;
$R_5$ represents a halogen atom or a cyano group, a $C_{1-6}$-alkoxy group, a $C_{1-6}$-fluoroalkyl group;
$R_6$ represents a phenyl group;
$R_2$ represents a hydrogen atom or $C_{1-6}$-alkyl group;
$R_3$ represents a hydrogen atom or a $C_{1-6}$-alkyl, $C_{3-7}$-cycloalkyl or $C_{3-7}$-cycloalkyl -$C_{1-3}$-alkyl group;
in the form of a base, addition salt with an acid or hydrate.

4. The compound of formula (I) as recited in claim 3 wherein:

$R_2$ represents a hydrogen atom;

$R_3$ represents a hydrogen atom or a $C_{1-6}$-alkyl, $C_{3-7}$-cycloalkyl or $C_{3-7}$-cycloalkyl -$C_{1-3}$-alkyl group.

5. A process for the preparation of a compound of formula (I) as recited in claim 1, comprising the conversion of the carbamate ester of general formula (II)

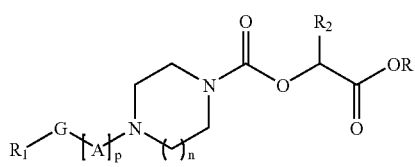

by aminolysis using an amine of general formula $R_3NH_2$ in which $R_1$, $R_2$, G, A, p and n are as defined in the general formula (I) according to claim 1 and R represents a methyl or ethyl group and in which $R_3$ is as defined in claim 1.

6. A process for the preparation of a compound of formula (I) as recited in claim 2 comprising the conversion of the carbamate-amide of general formula (V)

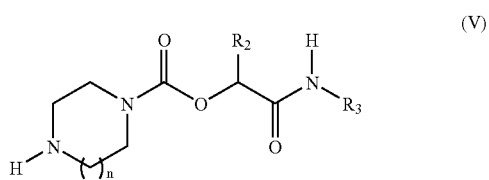

in which $R_2$, $R_3$ and n are as defined in the general formula (I) according to claim 1, by:

a) reacting the derivative of general formula $R_1$-G-$[A]_p$-W (IV), in which $R_1$, G, A, p and n are as defined in the general formula (I), with a carbonate of general formula (IIIa),

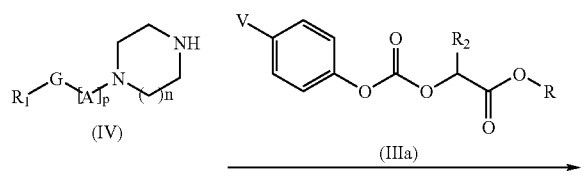

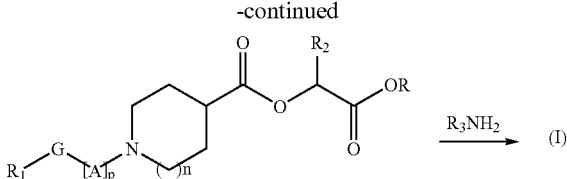

in which V represents a hydrogen atom or nitro group, $R_2$ is as defined in the general formula (I) and R represents a methyl or ethyl group;

b) converting the carbamate-ester of general formula (II) by aminolysis in a solvent using an amine of general formula $R_3NH_2$, in which $R_3$ is as defined in the general formula (I) and W represents a chlorine, bromine or iodine atom, or a mesylate or tosylate group.

7. A compound of the generic formula (II),

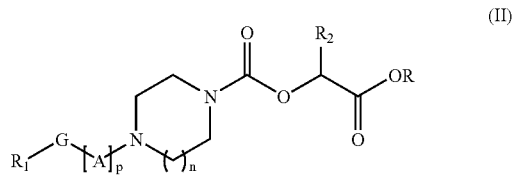

in which $R_1$, $R_2$, G, A, p and n are as recited in the general formula (I) according to claim 1 and R represents a methyl or ethyl group.

8. A pharmaceutical composition comprising at least one compound of formula (I) according to claim 1 in the form of a base, addition salt with an acid or pharmaceutically acceptable hydrate and optionally one or more pharmaceutically acceptable excipients selected from the group comprising carbohydrates, cellulose and cellulose derivatives, starches and starch derivatives, synthetic and natural polymers, sugars and sugar alcohols, gelatin, lipids, fats, lubricants and mixtures thereof.

* * * * *